(12) United States Patent
Samsoondar et al.

(10) Patent No.: US 7,328,052 B2
(45) Date of Patent: Feb. 5, 2008

(54) NEAR INFRARED RISK ASSESSMENT OF DISEASES

(75) Inventors: James Samsoondar, Cambridge (CA); Duncan MacIntyre, Campbellville (CA); Ashwani Kaushal, Mississauga (CA)

(73) Assignee: NIR Diagnostics Inc., Campbellville, Ontario (CA)

(*) Notice: Subject to any disclaimer, the term of this patent is extended or adjusted under 35 U.S.C. 154(b) by 320 days.

(21) Appl. No.: 10/943,737

(22) Filed: Sep. 17, 2004

(65) Prior Publication Data

US 2005/0075546 A1    Apr. 7, 2005

Related U.S. Application Data

(60) Provisional application No. 60/504,388, filed on Sep. 19, 2003.

(51) Int. Cl.
*A61B 5/00* (2006.01)
(52) U.S. Cl. ............................... 600/310; 600/344
(58) Field of Classification Search ................ 600/306, 600/309, 310, 322, 323, 344
See application file for complete search history.

(56) References Cited

U.S. PATENT DOCUMENTS

| | | | | |
|---|---|---|---|---|
| 5,247,931 A | * | 9/1993 | Norwood | 600/344 |
| 5,279,295 A | * | 1/1994 | Martens et al. | 600/335 |
| 5,348,002 A | * | 9/1994 | Caro | 600/310 |
| 5,361,758 A | | 11/1994 | Hall et al. | |
| 5,551,422 A | * | 9/1996 | Simonsen et al. | 600/322 |
| 5,786,592 A | * | 7/1998 | Hok | 600/310 |
| 6,040,578 A | | 3/2000 | Malin et al. | |
| 6,041,247 A | * | 3/2000 | Weckstrom et al. | 600/323 |
| 6,078,828 A | * | 6/2000 | Yasuda et al. | 600/310 |
| 6,236,047 B1 | | 5/2001 | Malin et al. | |
| 6,285,895 B1 | * | 9/2001 | Ristolainen et al. | 600/323 |
| 6,365,363 B1 | | 4/2002 | Parfenov et al. | |
| 7,043,287 B1 | * | 5/2006 | Khalil et al. | 600/310 |
| 7,043,288 B2 | * | 5/2006 | Davis et al. | 600/310 |
| 2002/0016534 A1 | * | 2/2002 | Trepagnier et al. | 600/316 |

FOREIGN PATENT DOCUMENTS

WO    WO 93/16629    9/1993

* cited by examiner

*Primary Examiner*—Eric F Winakur
(74) *Attorney, Agent, or Firm*—Morgan & Finnegan, LLP

(57) ABSTRACT

The present invention provides an apparatus and a method for identifying the risk of a clinical condition in a human or animal by correlating Near Infrared (NIR) absorbance spectral data with one or several parameters including a concentration of one or more substances in the skin, a concentration of one or more substances in skin plus subdermal tissue, a score derived from one or more clinical tests like a stress test on a treadmill, coronary angiography, or intravascular coronary ultrasound. The method determines the concentration of a compound in the skin of a human or animal and comprises the steps of placing a part of the skin against a receptor, directing electromagnetic radiation (EMR) from the near-infrared spectrum onto the skin, measuring a quantity of EMR reflected by, or transmitted through, the skin with a detector; and performing a quantitative mathematical analysis of the quantity of EMR to determine the concentration of the compound, for example free and esterfied cholesterol. An example of a clinical condition is cardiovascular disease.

13 Claims, 6 Drawing Sheets

NEAR INFRARED RISK ASSESSMENT OF DISEASES

This application claims the benefit of U.S. Provisional Application No. 60/504,388, filed on Sep. 19, 2003.

FIELD OF THE INVENTION

The present invention relates to an apparatus and a method of measuring the concentration of a compound in the skin of a subject, for example a human or animal. More particularly, the present invention relates to a method of determining a measured concentration of a compound in the skin, and optionally, to correlate the measured concentration of the compound to a specific clinical condition or to the propensity for a specific clinical condition.

BACKGROUND OF THE INVENTION

Clinical studies have revealed that the concentration of certain compounds in the skin of a subject may be used to assess the risk of development of specific medical conditions in that subject. Early detection of these types of risks in a patient permits measures to be taken that may slow or even prevent the onset of these conditions. As an example, it has been determined that elevated concentrations of cholesterol in the skin of an individual is an indication of a risk for cardiovascular disease. Therefore, the development of simple, non-invasive methods for determining the concentration of skin compounds is of importance.

In U.S. Pat. No. 6,365,363, Parfenov et al. describe a method of indirectly measuring the concentration of cholesterol in the skin of a subject by enzymatically oxidizing the cholesterol in a section of the subject's skin and then quantitating the amount of the hydrogen peroxide by-product stoichiometrically formed in this reaction using a second enzymatic reaction. As a complex series of enzymatic reactions are used in this method to indirectly determine the concentration of cholesterol, the method is both costly and prone to error. In addition, the development of a result using this method is time consuming.

In U.S. Pat. Nos. 6,236,047 and 6,040,578, Malin et al. describe a method for determining the concentration of a blood compound using light in the near-infrared range by analysing diffusively reflecting radiation emerging from the irradiated sample. However, there is no teaching in these patents as to the determination of concentrations of constituents in the skin of a subject.

Hall et al. also describe in U.S. Pat. No. 5,361,758 a non-invasive technique for directly measuring the concentration of constituents of blood using light in the near-infrared range. No specific methods for the determination of compounds within skin are provided.

It is an object of the invention to overcome disadvantages of the prior art.

The above object is met by the combinations of features of the main claims, the sub-claims disclose further advantageous embodiments of the invention.

SUMMARY OF THE INVENTION

The present invention relates to an apparatus and a method of measuring the concentration of a compound in the skin of a subject.

The present invention provides a method for determining the concentration of a compound in the skin of a human or animal comprising the steps of:

(a) placing a part of the skin against a receptor;

(b) directing electromagnetic radiation (EMR) from the near-infrared spectrum onto the skin;

(c) measuring a quantity of EMR reflected by, or transmitted through, the skin with a detector; and (d) performing a quantitative mathematical analysis of the quantity of EMR to determine the concentration of the compound.

According to one aspect of the present invention, there is provided a method for determining the concentration of an compound in the skin of a human or animal comprising the steps of:

(a) clamping off a part of said skin with a clamping means to remove blood from and reduce blood circulation to said part;

(b) directing a wavelength of light from the near-infrared spectrum onto the clamped-off part of said skin;

(c) measuring a quantity of light reflected by or transmitted through said part with a detector; and (d) performing a quantitative mathematical analysis of said quantity of light to determine the concentration of said compound.

According to another aspect, the present invention provides a method of identifying a clinical condition in need of treatment in a human or animal, the method comprising the steps of:

(a) clamping off a part of the skin of said human or animal with a clamping means to remove blood from and reduce blood circulation to said part;

(b) directing a wavelength of light from the near-infrared spectrum onto the clamped-off part of said skin;

(c) measuring a quantity of light reflected by or transmitted through said part with a detector;

(d) performing a quantitative mathematical analysis of said quantity of light to determine the concentration of an compound in said skin; and (e) correlating the concentration of said compound to the clinical condition in need of treatment by using a correlation algorithm.

According to a further aspect, the present invention provides a method for assessing the risk of a clinical condition in a human or animal, the method comprising the steps of:

(a) clamping off a part of the skin of said human or animal with a clamping means to remove blood from and reduce blood circulation to said part;

(b) directing a wavelength of light from the near-infrared spectrum onto the clamped-off part of said skin;

(c) measuring a quantity of light reflected by or transmitted through said part with a detector;

(d) performing a quantitative mathematical analysis of said quantity of light to determine the concentration of an compound in said skin; and.

(e) correlating the concentration of said compound to the risk of a clinical condition in need of treatment by using a correlation algorithm.

According to an even further aspect, the present invention provides a method of analyzing the skin of an animal to predict the ultimate taste or tenderness in meat derived from the animal, the method comprising the steps of:

(a) clamping off a part of the skin of said animal with a clamping means to remove blood from and reduce blood circulation to said part;

(b) directing a wavelength of light from the near-infrared spectrum onto the clamped-off part of said skin;

(c) measuring a quantity of light reflected by or transmitted through said part with a detector;

(d) performing a quantitative mathematical analysis of said quantity of light to determine the concentration of an compound in said skin; and (e) correlating the concentration of said compound to said taste or said tenderness by using a correlation algorithm.

The present invention also provides an apparatus comprising, a clamp having a first and a second end, the first end comprising one or more than one lever, and the second end comprising one or more than one receptor member to receive a sample of skin, wherein release of the one or more than one lever brings the one or more than one receptor member together over the sample of skin, the one or more than one receptor member house one or more than one input fiber optic elements for introducing an input electromagnetic radiation (EMR) to the skin sample, and one or more than one output optic fiber elements to remove an output EMR signal after interaction with one or more than one compounds within the skin. The input and output optic fiber elements may be adjacent each other within a fiber optic bundle within one receptor member, the input and output optic fiber elements may be located within separate receptor members.

This summary of the invention does not necessarily describe all necessary features of the invention but that the invention may also reside in a sub-combination of the described features.

BRIEF DESCRIPTION OF THE DRAWINGS

These and other features of the invention will become more apparent from the following description in which reference is made to the appended drawings wherein:

FIG. 1 shows a device for measuring compounds within skin.

FIG. 2 shows a close up of the portion of the device comprising the receptor members.

DESCRIPTION OF PREFERRED EMBODIMENTS

Figure 1A:
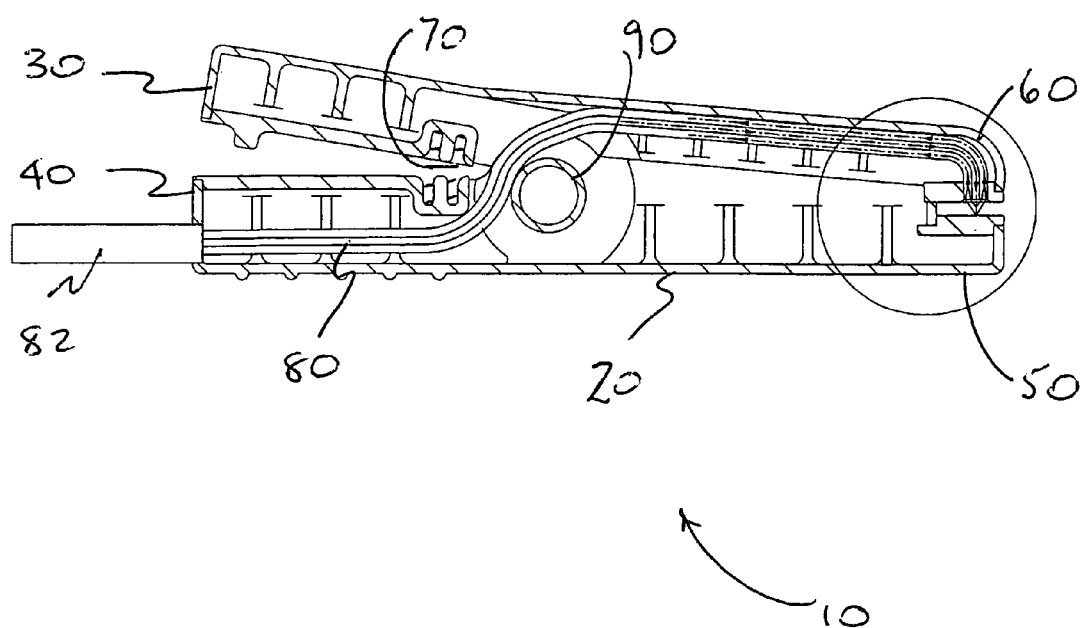
FIG. 1A shows a cross section of the device.

The present invention relates to an apparatus and a method of measuring the concentration of a compound in the skin of a subject, or in the skin plus subdermal tissue of a subject. More particularly, the present invention relates to a method of correlating NIR absorbance spectral data determined from skin, with a measured concentration of a compound, or scores generated from clinical tests, as a means of risk assessment for a specific clinical condition.

The following description describes preferred embodiments by way of example only and without limitation to the combination of features necessary for carrying the invention into effect.

The present invention provides an apparatus for non-invasive determination of the concentration of one or more compounds within the skin or the skin and subdermal tissue of a subject. The apparatus comprises a receptor shaped so that it can be placed in contact with a region of skin from a subject. A source electromagnetic radiation (EMR) is feed into the receptor, and following interaction with one or more than one compounds within the skin, the EMR is collected and analyzed. The apparatus may be as described below, or as known in the art, for example, but not limited to those disclosed in U.S. Pat. No. 5,361,758, WO 93/16629, U.S. Pat. No. 6,236,047 or U.S. Pat. No. 6,040,578 (all of which are incorporated herein by reference). The EMR that is collected after interaction with compounds within the skin may be either reflected from the skin, transmitted through the skin plus subdermal tissue, or both reflected from and transmitted through the skin depending upon the apparatus used.

The collected EMR signal is processed using the EMR data as independent variables, and any analyte value or scores from a clinical test as the dependent variable. The data processing uses mathematical techniques, for example but not limited to, simple linear regression, multiple linear regression, Partial Least Squares, Principal Component Regression, Neural Network, and Pattern Recognition, to develop one or more than one calibration algorithms to determine the concentration of one, or more than one target compounds within the skin sample, or a risk factor for a disease, for example but not limited to cardiovascular disease.

In the methods of the present invention, a part of the skin of a subject is brought into contact with a receptor for measurement of compounds within the skin. For some compounds, it may be preferred, but it is not required, that the blood content of the skin within the sample area is reduced. If reduced blood content of the skin is desired, the skin may be lightly pressed in any suitable manner, for example, a portion of skin may be clamped or pressed by the receptor. The area of the skin of the subject that is most preferably clamped is an area that is readily drained of blood. Examples, which are not meant to be limiting in any manner, of such an area include loose skin, for example the skin on the wrist, the palm, the neck, or the lobe of the ear. Examples of a receptor that can clamp an appropriate area of skin include receptors shaped as tweezers, tongs, or as a vice or pin, such as a spring-clamp. However, as indicated above, other devices that fit over an arm or leg, or that accept a finger etc. may also be used as described herein. Furthermore, a receptor that is placed, or pressed, against the skin may also be used to determine the concentration of a compound within the skin, by measuring diffuse reflection from the skin. The skin surface could also be brought into contact with a probe, for reflectance measurement.

Figure 1B:
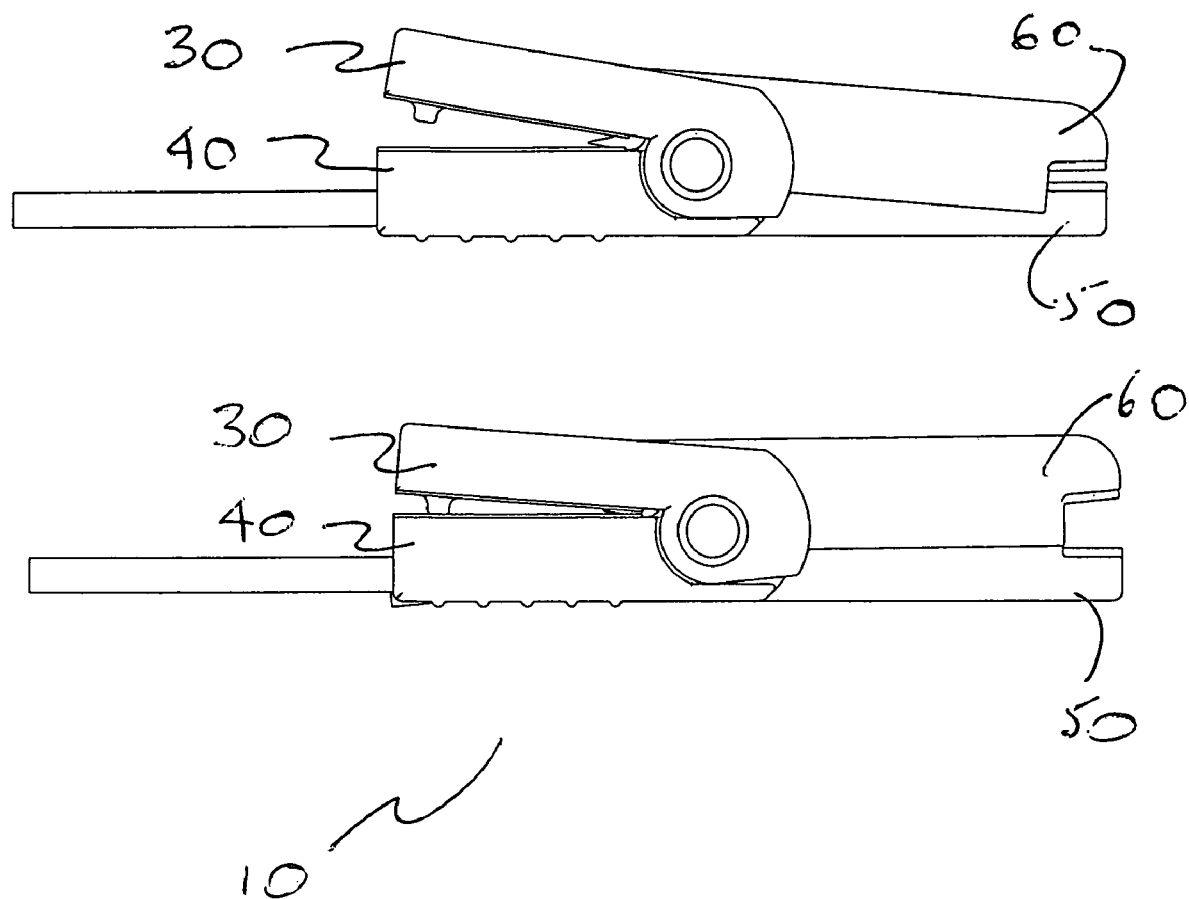
FIG. 1B shows two side views of the device. The upper figure shows the device where the receptor members are closed. The lower figure shows the device where the receptor members are open.

With reference to FIGS. 1A and B, there is shown a non-limiting example of an apparatus of the present invention (general indicated as 10) comprising a clamp-like device, for example, but not limited to a spring-clamp (20) having a first and a second end. The first end may be configured so that by pressing one or more than levers (30, 40 or 30 and 40), receptor members (50) and (60) open. Receptor members may be configured so that they pivot about element (90) to open, as indicated in FIG. 1B (lower figure), to receive a sample of skin (not shown in the figures for clarity), however, any method for opening receptor members (50) and (60) may be employed. Release of lever (30) or (40), or both, brings receptor members (50) and (60) together as shown in FIG. 1B (upper panel), and clamps the skin between members (50) and (60). Preferably, receptor members (50) and (60) are biased towards each other. A non-limiting example for biasing receptor members (50) and (60) together includes a spring (70), however, other methods of biasing may also be used. The amount of clamping pressure exerted on the skin may be adjusted as required for each skin sample.

Figure 2A:
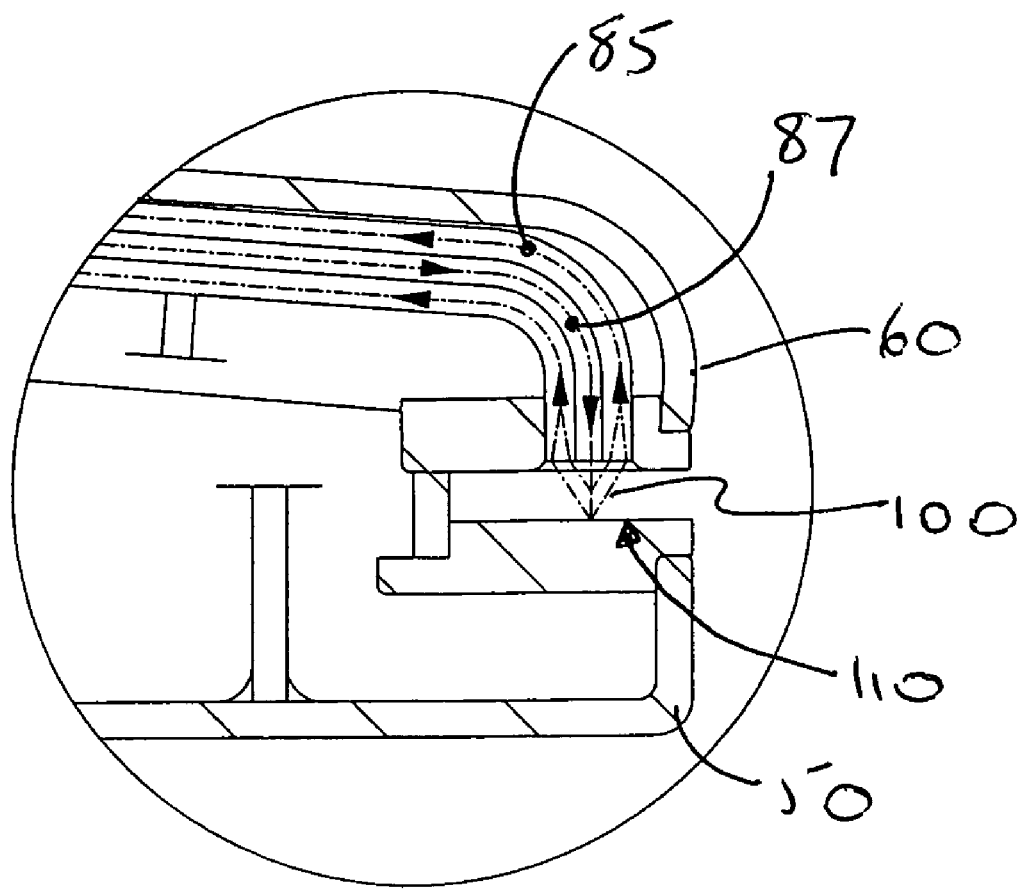
FIG. 2A shows a cross section view of the receptor members of FIG. 1.
Figure 3:
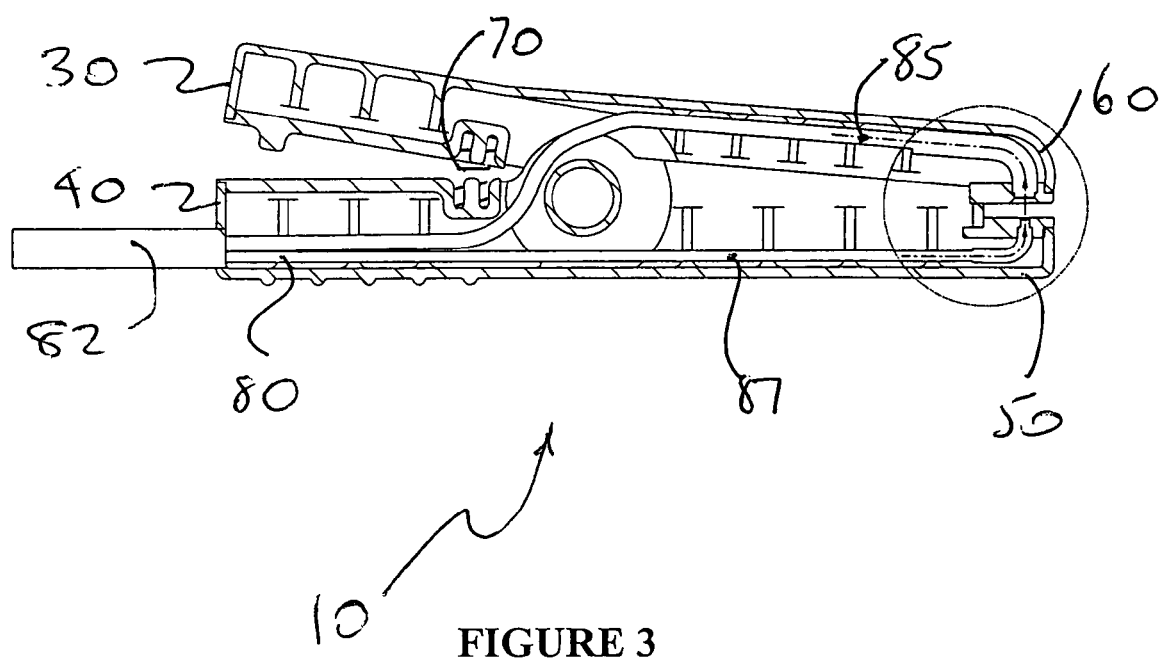
FIG. 3 shows a cross sectional view of an alternate device for measuring compounds within skin.

The apparatus as shown in FIG. 1 also comprises one or more than one fiber optic elements (80), as shown in more detail in FIG. 2A, that are used to introduce EMR to the skin sample (87), and to remove an output EMR signal (85) after interaction with one or more than one compounds within the skin. In the example shown in FIGS. 1 and 2A, the input (87) and output (85) elements reside adjacent each other within a fiber optic bundle (80) within one receptor member, for example receptor member (60). However, the input and output elements may also reside on both sides of the receptor members (50) and (60) as shown in FIG. 3. The input and output fiber optic elements are each made up of a plurality of fibers. The fiber optic bundle exits apparatus (20) at connector (82).

The receptor members (50) and (60), and the fiber optic elements (87) and (85) of FIG. 1 are shown in more detail in FIG. 2A. After a skin sample (which not shown for clarity in FIG. 2A) is placed between receptor members (50) and (60), EMR is introduced via fiber optic element (87) to the sample. The path of the EMR is shown as (100) in FIG. 2A. The input EMR may:
1) reflect from the skin sample after interacting with compounds within the skin, and enter output fiber optic (85);
2) transmit through skin sample to a reflective base (110) placed on the opposite receptor member from that housing the fiber optic elements and re-transmit through the skin sample to output optic fiber (85). In the case shown in FIG. 2A, the reflective base (110) is placed on receptor member (50), and the fiber optic elements are housed within receptor member (60).
3) both transmit through the skin and reflect from the skin after interacting with compounds within the skin.

Figure 2B:
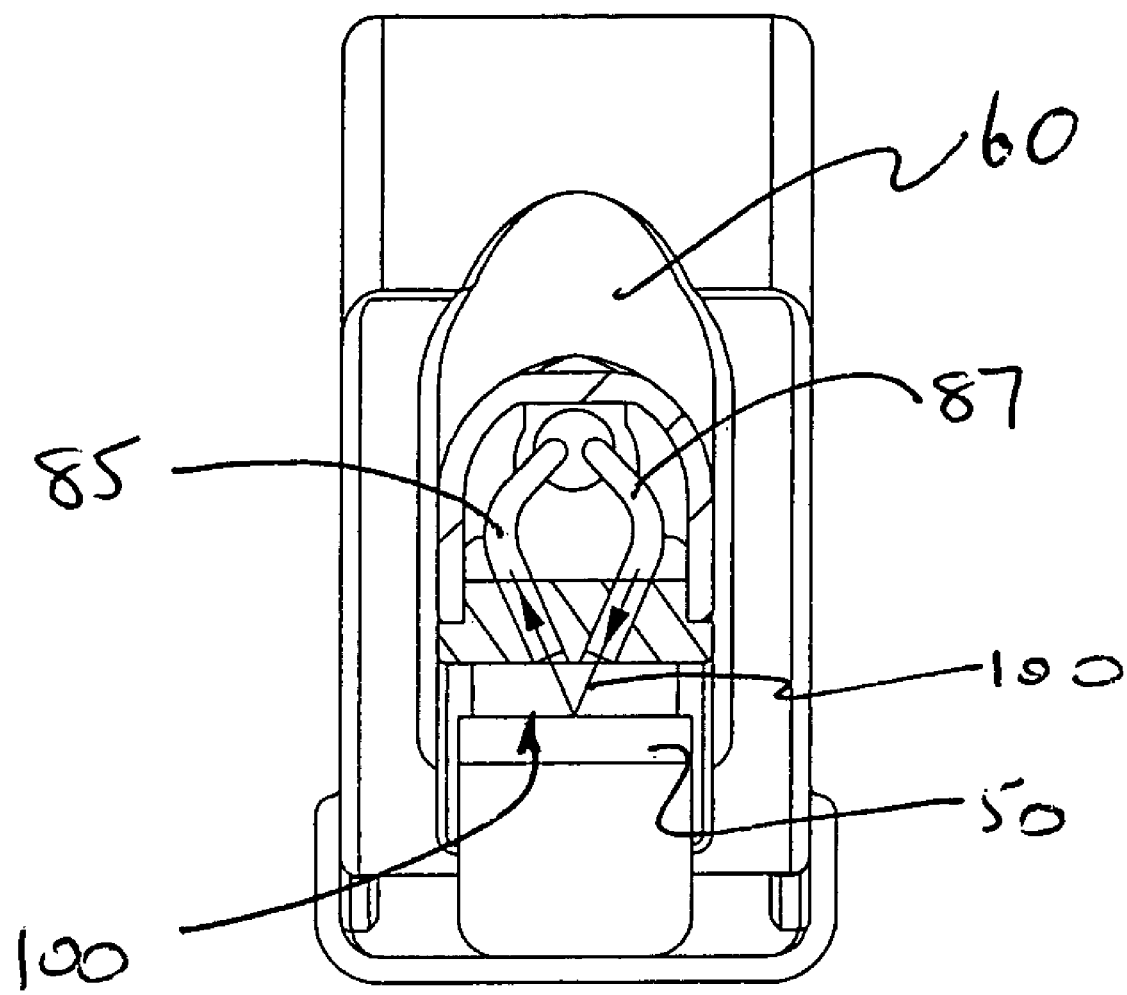
FIG. 2B shows a front view of the receptor members of FIG. 1.

The input and output fibers (87 and 85, respectively) may be offset with respect to each other as shown in FIG. 2B.

With reference to FIG. 3, there is shown an alternate apparatus of the present invention (generally shown as 10) comprising a spring-clamp (20) as described above with reference to FIG. 1. In this alternated apparatus, fiber optic bundle (80) comprising input and output fiber optic elements, splits so that input fiber optic element (87) is housed within one receptor member, for example (50), and output fiber optic element (85) is housed within another receptor member, for example (60), however, the input and output orientation of the fiber optic elements may also be reversed. The light path in this alternate apparatus is configured to pass from the input fiber (87), through a skin sample placed between receptor members (50) and (60) to the output fiber (85).

The size of the opening between receptor members (50) and (60) may vary to accommodate various thicknesses of skin sample.

Figure 4:
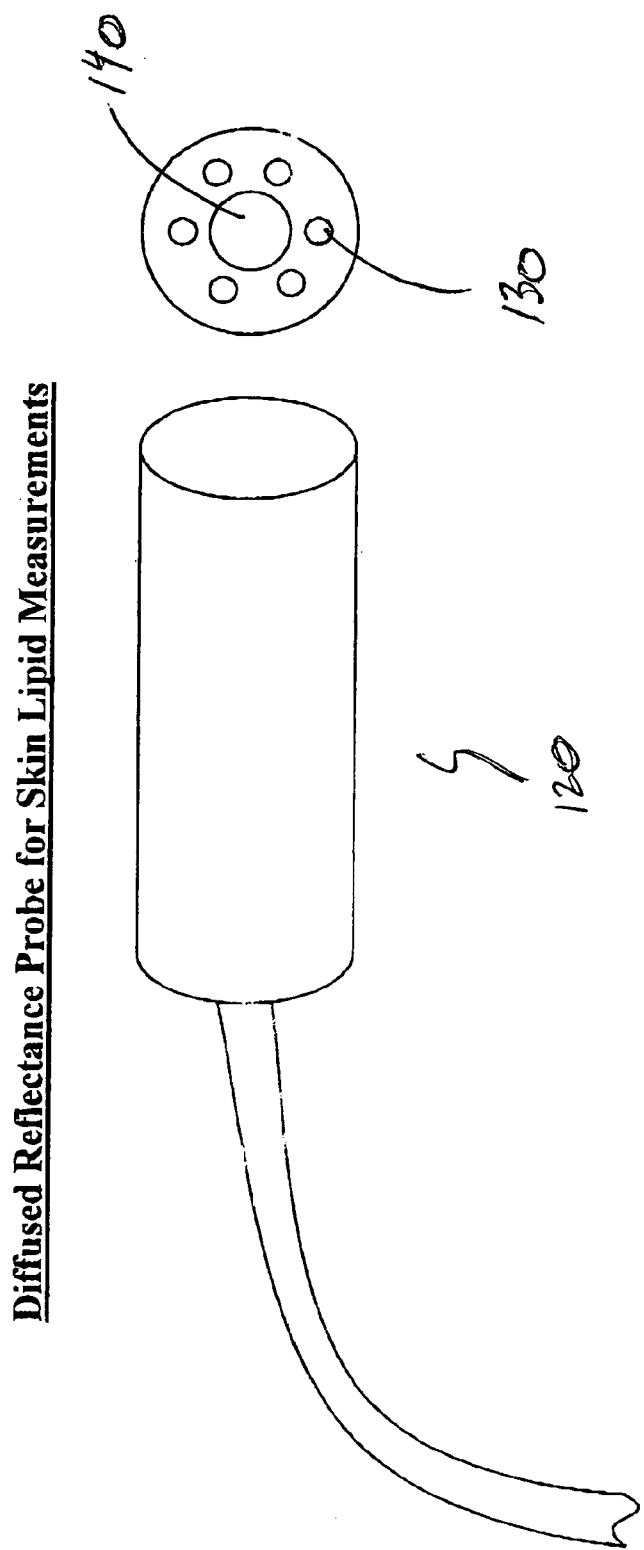
FIG. 4 shows an alternate device for measuring compounds within the skin.

A receptor of the present invention may also comprise a single sided probe that can make contact with a skin sample, for example, generally shown as (120) in FIG. 4. Such a probe may comprise concentric rings of optic fibers so that each ring is made up by fibers carrying either input or output EMR. If the inner ring (140) of fibers is carrying input EMR, then the outer ring (130) of fibers may carry the output signal, or visa versa. This type of probe may be used to determine the concentration of a compound within the skin using reflectance. During use, the probe may be placed against the skin of the hand, arm, back or elsewhere. If desired the probe may be pressed against the skin to partially displace blood from the skin sample.

Alternate configurations of an apparatus may also be used for the determination of a compound within a skin sample as described herein, including, but not limited to those described in U.S. Pat. No. 5,361,758, WO 93/16629, U.S. Pat. No. 6,236,047 or U.S. Pat. No. 6,040,578 (all of which are incorporated herein by reference). Modification of the calibration algorithms used to determine the concentration of one or more compounds of interest within each of these devices are be required so as to ensure that compounds within the skin are preferentially determined, as opposed to components within the blood.

Preferred examples of compounds that are measured according to the present invention are selected from the group consisting of fats, proteins, including cell-surface proteins, glycoproteins, lipoproteins, carbohydrates, and steroids. The compound is most preferably a steroid such as cholesterol. Furthermore, cholesterol is present at higher concentration within the skin than in blood, thereby reducing background cholesterol levels associated with blood in skin sample cholesterol determinations.

The present invention uses a correlation step to relate the measurements of transmitted or reflected light to a concentration value for one or more than one given compounds. If desired, the measured concentration of the compound may be related to a particular parameter such as a clinical condition in need of treatment. The correlation steps used in the methods of this invention may involve several steps of linear regression analysis.

The concentration of a given compound is preferably calculated according to the present invention by using a calibration equation derived from a statistical analysis, for example but not limited to a least squares best fit, of a plot of the values of concentration of a calibration set of samples of the compound, which are determined using the method of the present invention, versus the values of the concentration of the calibration set measured directly by a different method. Any known method for determining the concentration of one or more compounds may be used as would be known to one of skill in the art.

In one aspect of the present invention, there is provided a method that identifies a clinical condition in a human or animal by correlating the concentration of a measured compound in the skin of the human or animal to a clinical condition in need of treatment using a correlation algorithm. In this case, the correlation algorithm determines the correlation between the concentration of the compound and a positive result from a medical test that screens for a particular clinical condition.

In another aspect of the present invention, there is provided a method that identifies the risk of a clinical condition in a human or animal by correlating the concentration of a measured compound in the skin of a human or an animal to the risk of a clinical condition in need of treatment using a correlation algorithm. In this case, the correlation algorithm determined the correlation of the concentration of the compound to a result from a medical test that screens for a particular clinical condition, which approaches a positive result.

Examples of the medical test mentioned above include coronary angiography, stress test, intravascular coronary ultrasound, flow-mediated brachial vasoactivity, and carotid sonography.

The near infrared region of the electromagnetic spectrum is generally considered to be the spectral interval extending from 650 nm through to 2700 nm and measurements of samples as described herein are preferably taken from about 700 nm to about 1100 nm, or from about 900 nm to about 1600 nm, or from about 1300 nm to about 2500 nm. Absorption bands observed in this interval are primarily the combination and overtone bands of the fundamental infrared bands. Although very weak in intensity, being typically less than one-tenth in intensity of the fundamental infrared bands, these bands are considered to be analytically useful because nearly all chemical species exhibit characteristic absorption bands in this spectral interval. The near infrared region is particularly well-suited to in vivo diagnostic applications because human tissue is essentially transparent to the incident radiation and therefore sufficient penetration of the radiation is possible to allow accurate quantitative analysis.

The source of EMR used in the present invention is preferably near-infrared light, for example but not limited to a polychromatic light source. This type of light source can emit light over a very wide bandwidth including light in the near infrared spectrum. In this case, the light from the light source preferably passes first through a collimator, which is a collection of lenses that concentrate the light into a narrow parallel beam directed at the receptor.

The polychromatic light source can be a quartz-halogen or a tungsten-halogen bulb and is powered by a stabilized power source, for example, a DC power supply, or by a battery. Preferably, the linear array detector has at least ten elements. This polychromatic light source may be a tungsten-halogen lamp or it may be a collection of LEDs or other light sources selected to emit radiation in the range of 650 to 1100 nm.

A receptor is preferably used which is shaped to receive a part of the subject for sampling, for example a clamped part of the skin. Alternatively, the receptor could be shaped so that the part of the human or animal, onto which the EMR is to be directed, is placed near the receptor rather than within the receptor. In any event, the sampled part of the skin is in close contact with the receptor.

The EMR is directed onto, and dispersed by, the skin sample of the subject. The dispersed light is collected by using any suitable method for example fiber optics, or lenses, and the output signal directed to a diffraction device that separates the wavelengths of light within the output signal into their component parts. Examples of a diffraction device include but are not limited to a diffraction grating or a holographic grating.

The collected signal can comprise EMR that has passed through the skin sample of the subject or has reflected off the skin sample, or a combination thereof. Preferably, the collected EMR has passed through the skin sample. The diffracting device preferably disperses the EMR into its component wavelengths so that the infrared region falls along the length of a detector such as, but not limited to a linear array detector (e.g. a 256 element photo diode array), or a CCD. In the case of an array, the detector has a series of diodes and is preferably electronically scanned by a microprocessor to measure the charge accumulated on each diode, the charge being proportional to the intensity of EMR for each wavelength transmitted through or reflected from the tissue in the receptor. The detector is connected to the microprocessor, producing an output spectrum, with the microprocessor analyzing the measurements and ultimately producing a result for each concentration level determined. The result can be stored, shown on a display, or printed on a printer. A keyboard allows a user to control the device, for example, to specify a particular constituent to be measured. The timing and control is activated by the microprocessor to control the device, for example, to determine number and timing of measurements.

After measurements are obtained for the transmittance, reflectance or both, the log of the inverse of these measurements is preferably taken, that is, log 1/T and log 1/R, where T and R represent the transmittance and reflectance respectively. Both log 1/T and log 1/R are referred to as absorbance measurements. A reference set of measurements is taken of the incident light, being the light generated in the device when no part of the subject is in contact with the receptor. The absorbance is then calculated when a part of the subject is in contact with the receptor as a ratio of measurements compared to the reference set of measurements. In the case of reflectance measurement, the reference EMR measurement is the EMR reflected off a surface like ceramic, which diffusely reflects most of the light. In both transmittance and reflectance modes, the apparatus can be configured as a single beam or dual beam system.

The second derivative of the measurements is preferably taken in order to reduce any variation in the result that will be caused by a change in path length for the light caused by measuring the compound concentration in different thicknesses of the skin sample. While there are other means of manipulating the data obtained from the measurements of reflectance and transmittance which will produce the same results as that obtained by taking the second derivative, the taking of the second derivative is the preferred means.

As the results obtained can vary with the temperature of the part of the subject, the device used in the method of the present invention preferably contains a temperature sensor so that the temperature of the analyzed clamped-off part can be measured rapidly at the time of the spectral sampling. This temperature sensor is typically a small-mass thermocouple. Computer software can then be used to allow the microprocessor to compensate for spectrum deviations due to the temperature. So as not to delay the production of results, the temperature sensor preferably has a 150 to 200 millisecond response time.

The linear array detector is preferably a photo diode array that is positioned to intercept, across its length, the dispersed spectrum from the diffraction grating. The microprocessor is directed by software to scan the linear array detector and calculate the second derivative of the spectrum computed. The microprocessor can then calculate the concentration of the particular constituents being measured using the absorbance and second derivative values for a number of selected wavelengths. A calibration equation is preferably used for each constituent and is determined by the compound being measured.

The use of the second derivative calculation also eliminates base line shifts due to different path lengths or absorbing water bands, and in addition, enhances the separation of overlapping absorption peaks of different constituents of the mixture being analyzed.

The microprocessor can collect up to one hundred spectra and can then immediately calculate the second derivative of the averaged results. Preferably, the results will be digitally displayed for the user. Also, by using the memory capacity of the microprocessor, a user can monitor trends by comparing the most recent result with previous results.

While the device of the present invention can be designed to measure one constituent, the device can also be designed to measure several constituents simultaneously.

The above description is not intended to limit the claimed invention in any manner, furthermore, the discussed combination of features might not be absolutely necessary for the inventive solution.

The present invention will be further illustrated in the following examples. However it is to be understood that these examples are for illustrative purposes only, and should not be used to limit the scope of the present invention in any manner.

All citations are herein incorporated by reference.

The present invention has been described with regard to preferred embodiments. However, it will be obvious to persons skilled in the art that a number of variations and modifications can be made without departing from the scope of the invention as described herein.

The embodiments of the invention in which an exclusive property of privilege is claimed are defined as follows:

1. A method of identifying a clinical condition in need of treatment in a human or animal, the method comprising the steps of:
   (i) determining the concentration of an analyte selected from the group consisting of a fat, a lipoprotein, and a steroid in the skin of the human or animal by a method comprising:
      (a) placing a part of the skin against a receptor in a manner that removes a portion of the blood within the skin;
      (b) directing electromagnetic radiation (EMR) from the near-infrared spectrum onto the skin;
      (c) measuring a quantity of EMR reflected by, or transmitted through, the skin with a detector; and
      (d) performing a quantitative mathematical analysis of the quantity of EMR to determine the concentration of the analyte; and
   (ii) correlating the concentration of the analyte to the clinical condition in need of treatment, using a correlation algorithm.

2. The method of claim 1, wherein the analyte is free cholesterol.

3. The method of claim 1, wherein the analyte is esterfied cholesterol.

4. The method of claim 1, wherein the analyte is total cholesterol.

5. The method of claim 1, wherein in the step of placing (step (a)), the receptor presses against the skin thereby removing a portion of the blood within the skin.

6. The method of claim 1, wherein in the step of placing (step (a)), the receptor is clamped against the skin thereby removing a portion of the blood within the skin.

7. A method for assessing the risk of a clinical condition in a human or animal, the method comprising the steps of:
   (i) determining the concentration of an analyte selected from the group consisting of a fat, a lipoprotein, and a steroid in the skin of the human or animal by a method comprising:
      (a) placing a part of the skin against a receptor in a manner that removes a portion of the blood within the skin;
      (b) directing electromagnetic radiation (EMR) from the near-infrared spectrum onto the skin;
      (c) measuring a quantity of EMR reflected by, or transmitted through, the skin with a detector; and
      (d) performing a quantitative mathematical analysis of the quantity of EMR to determine the concentration of the analyte; and
   (ii) correlating the concentration of the analyte to the risk of a clinical condition in need of treatment by using a correlation algorithm.

8. The method of claim 7, wherein the analyte is free cholesterol.

9. The method of claim 7, wherein the analyte is esterfied cholesterol.

10. The method of claim 7, wherein the analyte is total cholesterol.

11. The method of claim 7, wherein in the step of placing (step (a)), the receptor presses against the skin thereby removing a portion of the blood within the skin.

12. The method of claim 7, wherein in the step of placing (step (a)), the receptor is clamped against the skin thereby removing a portion of the blood within the skin.

13. An apparatus comprising:
   a clamp having a first and a second end, the first end comprising one or more than one lever, and the second end comprising two receptor members to receive a sample of skin,
   wherein release of the one or more than one lever brings the two receptor members together over the sample of skin,
   wherein one of the two receptor members houses one or more than one input fiber optic element for introducing an input electromagnetic radiation (EMR) to the sample of skin, and one or more than one output fiber optic element to remove an output EMR signal after interaction with one or more than one analyte within the sample of skin,
   wherein the other of the two receptor members has a reflective base that reflects EMR radiation transmitted through the sample of skin when placed between the two receptor members to the one or more than one output fiber optic element, and
   wherein the one or more than one input fiber optic element and the one or more than one output fiber optic element are adjacent to each other within a fiber optic bundle.

* * * * *